United States Patent [19]

Olney

[11] Patent Number: 4,833,148

[45] Date of Patent: May 23, 1989

[54] METHOD OF USING ALKENYL- OR ALKYNYL-SUBSTITUTED THIOBARBITURATES TO REDUCE NEUROTOXIC INJURY

[75] Inventor: John W. Olney, Laude, Mo.

[73] Assignee: Washington University, St. Louis, Mo.

[21] Appl. No.: 36,500

[22] Filed: Apr. 9, 1987

[51] Int. Cl.$^4$ ............................................. A61K 31/19
[52] U.S. Cl. ................................................... 514/270
[58] Field of Search ........................................ 514/270

[56] References Cited

U.S. PATENT DOCUMENTS 3,930,006 12/1975 Wiggins et al. ..................... 514/270

FOREIGN PATENT DOCUMENTS 692421 6/1953 United Kingdom .

OTHER PUBLICATIONS

Merck Index p. 1207 9th Ed. (1976).

*Primary Examiner*—Stanley J. Friedman
*Attorney, Agent, or Firm*—J. Timothy Keane; Paul D. Matukaitis

[57] ABSTRACT

Methods and compositions are described for treatment to control brain damage associated with anoxia or ischemia which typically follows stroke, cardiac arrest or perinatal asphyxia. The treatment includes administration of an alkenyl-substituted or alkynyl-substituted thiobarbiturate characterized in having broad-spectrum activity as an antagonist to inhibit excitotoxic actions at major neuronal excitatory amino acid receptor sites.

5 Claims, No Drawings

METHOD OF USING ALKENYL- OR ALKYNYL-SUBSTITUTED THIOBARBITURATES TO REDUCE NEUROTOXIC INJURY

FIELD OF THE INVENTION

This invention is in the field of clinical neurology and relates specifically to methods and compositions for neuroprotective purposes such as controlling brain damage which occurs during periods of anoxia or ischemia associated with stroke, cardiac arrest or perinatal asphyxia.

BACKGROUND OF THE INVENTION

Unlike other tissue which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system. Glutamate (Glu) is an endogenous amino acid which was early characterized as a fast excitatory transmitter in the mammalian brain. Glutamate is also known as a powerful neurotoxin capable of killing CNS neurons under certain pathological conditions which accompany stroke and cardiac arrest. Normally, glutamate is maintained at relatively high concentrations within brain tissue cells by energy-consuming transport systems. Under low energy conditions which occur during conditions of hypoglycemia, hypoxia or ischemia, these cells can release glutamate and under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockade of synaptic transmission or by the specific antagonism of postsynaptic glutamate receptors [see S. M. Rothman and J.W. Olney, "Glutamate and the Pathophysiology of Hypoxia-Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Certain oxobarbiturate and thiobarbiturate compounds, including thiopentone (thiopental), have been studied for their convulsant, anticonvulsant and anesthetic properties, with both series of barbiturates found to have the same qualitative activities [P. R. Andrews, et al., *Eur. J. Pharmacol.*, 79, 61–65 (1982)]. High-dose barbiturate treatment, with compounds such as thiopental, pentobarbital and phenobarbitol, has been reported as a potentially beneficial approach to clinical management of cerebral anoxia-ischemia [J. H. Piatt, Jr., et al. *Neurosurgery*, Vol. 15, No. 3, 427–444 (1984)]. Glutamate antagonists have been used in various animal models to treat epilipsy-related conditions [B. Meldrum *Clinical Sci.*, 68, 113–122 (1985)].

It is known that certain barbiturates protect the ex vivo chick embryo retina from the excitotoxic activity of either N-methyl aspartate (NMA) or kainic acid (KA). For example, barbiturates such as aprobarbital, phenobarbital, pentothal, seconal and amytal have been shown to possess anti-excitotoxic activity, with seconal having the most potency. The anti-excitotoxic actions of barbiturates in the chick embryo retina cannot readily be attributed to an action through the gamma-aminobutyric acid (GABA) system since GABA itself, in very high concentrations, does not protect retinal neurons against the toxic actions of NMA, KA or GLu. ThE acute anti-excitotoxic properties of several short-acting barbiturates (methohexital, thiopental, thiamylal) have been demonstrated in the ex vivo chick embryo retina. It is believed that because of such anti-excitotoxic properties, these short-acting barbiturates prevent KA from causing seizures and seizure-related brain damage (SRBD) in the in vivo rat.

Other classes of compounds have been tested as agonists in blocking NMDA- or KA-induced neurotoxicity [J. W. Olney eT al., "The Anti-Excitotoxic Effects of Certain Anesthetics, Analgesics and Sedative-Hypnotics," *Neuroscience Letters*, 68, 29–34 (1986)]. The tested compounds included phencylidine, ketamine, cyclazocine, kynurenate and various barbiturates such as secobarbital, amobarbital and pentobarbital. None of the tested compounds was reported as a broad spectrum antagonist effective in blocking the neurotoxic actions of NMA, KA, quisqualate and glutamate.

DESCRIPTION OF THE INVENTION

Control of neuropathological processes and the neurodegenerative consequences thereof in mammals is provided by treating a mammal susceptible to neurotoxic injury with an anti-excitotoxic composition comprising an effective amount of a broad-spectrum neuroreceptor antagonist. The antagonist is characterized in having broad spectrum activity as an antagonist at major neuronal excitatory amino acid receptor sites to inhibit excitotoxic actions at such major receptor sites. This broad-spectrum antagonist is provided by a thiobarbiturate compound characterized in having at least one ring atom substituted with a group containing at least one carbon-to-carbon bond unsaturated moiety. Examples of groups containing such unsaturated moiety are alkenyl groups and alkynyl groups.

A family of alkenyl- or alkynyl-substituted thiobarbiturate compounds for use in this method of treatment is defined by Formula I:

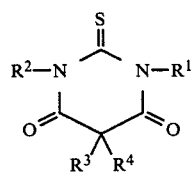

wherein each of $R^1$, $R^2$, $R^3$ and $R^4$ groups is independently selected from hydrido, linear or branched alkyl groups of one to twenty carbon atoms, linear or branched alkenyl groups of two to twenty carbon atoms, linear or branched alkynyl groups of two to twenty carbon atoms, phenyl, benzyl, and oxygen- or nitrogen-containing heterocyclic of three to ten ring atoms, any one of which $R^1$, $R^2$, $R^3$ and $R^4$ groups may be optionally substituted at a substitutable position by one or more of oxo, hydroxyl, alkoxy, thio, amino, halo, carboxyl, carboxamido and thiocarboxamido substituents, with the proviso that at least one of said $R^1$, $R^2$, $R^3$ and $R^4$ groups is an alkenyl group or an alkynyl group, or is a group substituted with at least one alkenyl moiety or alkynyl moiety. Specific examples of alkyl groups are methyl, ethyl, n-propyl, isopropyl, n-butyl, sec-butyl, iso-butyl, tert-butyl, n-pentyl, iso-pentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within substituents for attachment at the $R^1$ through $R^4$ positions are generic groups such as hydroxyalkyl, hydroxyalkenyl, hydroxyalkynyl, hydroxyphenyl, hydroxybenzyl, alkoxyalkyl, thioalkyl, alkylthioalkyl, thioalkenyl, thioalkynyl, allyl, aminoalkyl, aminoalkenyl, aminoalkynyl, haloalkyl and haloalkynyl, wherein any one or more halo atoms may be substituted at any one or more of the alkyl, alkenyl or alkynyl carbon atoms. An example of haloalkenyl is bromoallyl. Examples of oxygen- or nitrogen-containing heterocyclic groups are furyl, furfuryl, thienyl and cycloamido.

Thiobarbiturate compounds of particular interest arE those wherein each of $R^1$ and $R^2$ is hydrido and each of $R^3$ and $R^4$ is independently selected from methyl, ethyl, n-propyl, isopropyl, n-butyl, sec-butyl, iso-butyl, tert-butyl, methylbutyl, thiobutyl, ethenyl, propenyl, butenyl, pentenyl, pentynyl, furfuryl, chloroallyl, bromoallyl, azepinyl, azepinylmethyl, 3-chloro-2-butenyl, butoxymethyl, 5-iodo-4-pentenyl, 1-methyl-2-butenyl, 2-(butylthio)ethyl, 3-ethyl-1,2-pentadienyl, 3-hydroxy-1-methylbutyl, 2-oxo-1-pyrrolidinylmethyl, isobutoxymethyl, isobutoxymethoxyethyl, 2-mercaptoethyl, 2-furanylmethyl and 1-methyl-2-pentynyl.

Included within the family of compounds of Formula I are the tautomeric forms of the described compounds, isomeric forms including diastereomers, and the pharmacologically-active salts thereof.

Specific alkenyl-substituted and alkynyl-substituted thiobarbiturate compounds of interest within the Formula I family are as follows:

5-ethyldihydro-1-methyl-5-(1-methyl-2-pentynyl)-2-thioxo-4,6(1H,5H)-pyrmidinedione;
5-allyl-1-methyl-5-(1-methyl-2-pentynyl)-2-thio-barbituric acid;
5-allyl-5-(1-methyl-2-pentynyl)-2-thio-barbituric acid;
5-allyl-5-furfuryl-2-thio-barbituric acid;
5-(3-furanylmethyl)dihydro-5-(2-propenyl) -2-thioxo-4,6-(1H,5H)-pyrimidinedione;
5-(2-chloroallyl)-5-[[(isobutylmethoxy) methyl]methyl]-2-thio-barbituric acid;
5-(2-chloroallyl)-5-[[(isobutoxymethyl)-2-thio-barbituric acid;
5-allyl-5-(1-methyl-2-pentynyl)-2-thio-barbituric acid, sodium salt;
dihydro-5-(2-propenyl)-5-tetradecyl-2-thioxo-4,6(1H,5H)-pyrimidinedione;
5-(2-bromoallyl)-5-[(isopentyloxy)methyl]-2-thio-barbituric acid;
5-allyl-5-(1-methylbutyl)-2-thio -barbituric acid;
5-allyl-5-8 (hexahydro-2-oxo-1H-azepin-2-yl)methyl]-2thio-barituric acid;
5-allyl-5-[(b 2-oxo-1-pyrrolidinyl)methyl]-2-thio-barbituric acid;
5-(3-chloro-2-butenyl)-5-[(hexahydro-2-oxo-1H-azepin-2-yl)-methyl]-2thio-barbituric acid;
5,5-diallyl-2-thiobarbituric acid;
dihydro-5-(3-hydroxy-1methylbutyl)-5-(2-propenyl)-2-thioxo-4,6(1H, 5H) -pyrimidinedione;
5-butyl-5-ethyldihydro-2-thioxo-, monosodium salt 4,6(1H, 5H)-pyrimidinedione;
dihydro-5-(phenylmethyl)-5-(2-propenyl)-2-thioxo-4,6(1H,5H)-pyrimidinedione, monosodium salt;
dihydro-5-(methylpropyl)-5-(2-propenyl)-2-thioxo-4,6(1H,5H)-pyrimidinedione, monosodium salt;
hexahydro-δ-methyl-4,6-dioxo-5-(2-propenyl) -2-thioxo-methyl-5-pyrimidinebutanoate;
5-ethyl-5-(3-ethyl-1,2-pentadienyl)dihydro-2-thioxo-4,6-(1H,5H) -pyrimidinedione;
hexahydro-δ-methyl-4,6-dioxo-5-(2-propenyl) -2-thioxo-5-pyrimidinebutanoic acid;
5,5-diethyldihydro-1-(2-propenyl)-2-thioxo-4,6(1H,5H)-pyrimidinedione;
5-(2-butenyl)dihydro-5-(1methylpropyl)-2-thioxo-4,6(1H,5H)-pyrimidinedione, monosodium salt;
[(hexahydro-4,6-dioxo-2-thioxo-5-pyrimidinyl)methylene]-propanedinitrile;
1-cyclohexyldihydro-3-phenyl-5,5-di-2-propenyl-2-thioxo-4,6(1H,5H)-pyrimidinedione;
dihydro-5-(1-methylethyl)-5-(2-propenyl)2-thioxo-4,6(1H,5H)-pyrimidinedione;
5-dodecyldihydro-5-(2-propenyl)-2-thioxo-4,6(1H,5H)-pyrimidinedione;
5-ethenyldihydro-5-(1-methyl-2-pentynyl)-2-thioxo-4,6(1H,5H) -pyrimidinedione;
5-ethyldihydro-5-(1methyl-2-butenyl)-2-thioxo-4,6(1H,5H)-pyrimidinedione;
5-ethyldihydro-5-(5-iodo-4-pentenyl)-2-thioxo-4,6(1H,5H)-pyrimidinedione;
5-(2-butenyl)-5-(2-butenyl)-5-(2-mercaptoethyl)-2-thio-barbituric acid;
5-allylhexahydro-δ-methyl-4,6-dioxo-2-thioxo-5-pyrimidinebutyric acid;
5-(butoxymethyl)-5-(2-chloroallyl)-2-thio-barbituric acid;
5-ethyl-1-methyl-5(1-methyl-2-pentynyl)-2-thio-barbituric acid;
5-(2-chloroallyl)-5-(p-methoxybenzyl)-2-thio-barbituric acid;
5-(2-chloroallyl)-5-[p-(isopentyloxy)benzyl]-2thio-barbituric acid;
5-allyl-5-hexadecyl-2-thio-barbituric acid;
5-allyl-2-thio-5-tridecyl-barbituric acid;
5-(2-bromoallyl)-5-isopropyl-2-thio -barbituric acid;
5-(3-chloro-2-butenyl)-5-ethyl-2-thio-barbituric acid;
5,5-diallyl-1,3-dimethyl-2-thio-barbituric acid;
5-allyl-5-isopentyl-2-thio-barbituric acid;
5-allyl-5-(2,2-dimethylbutyl)-2-thio-barbituric acid;
5-(2-butenyl)-5-(1-methylbutyl)-2-thio-barbituric acid;
5-allyl-1-butyl-5-sec-butyl-2-thio-barbituric acid;
5-allyl-5-(2-methylbutyl)-1-propyl-2-thio-barbituric acid;
5,5-diallyl-1-isopentyl-2-thio-barbituric acid;

5-ethyl-5-[2-hydroxy-1-methylpropyl]-2-thio-barbituric acid;

α[2-(hexahydro-4,6-dioxo-2-thioxo-5-pyrimidinyl)-vinyl]-tetrahydro-4,6-dioxo-2-thioxo-Δ5(2H)-α-pyrimidineacetic acid.

Of particular interest are allyl-substituted thiobarbiturates having the following structures:

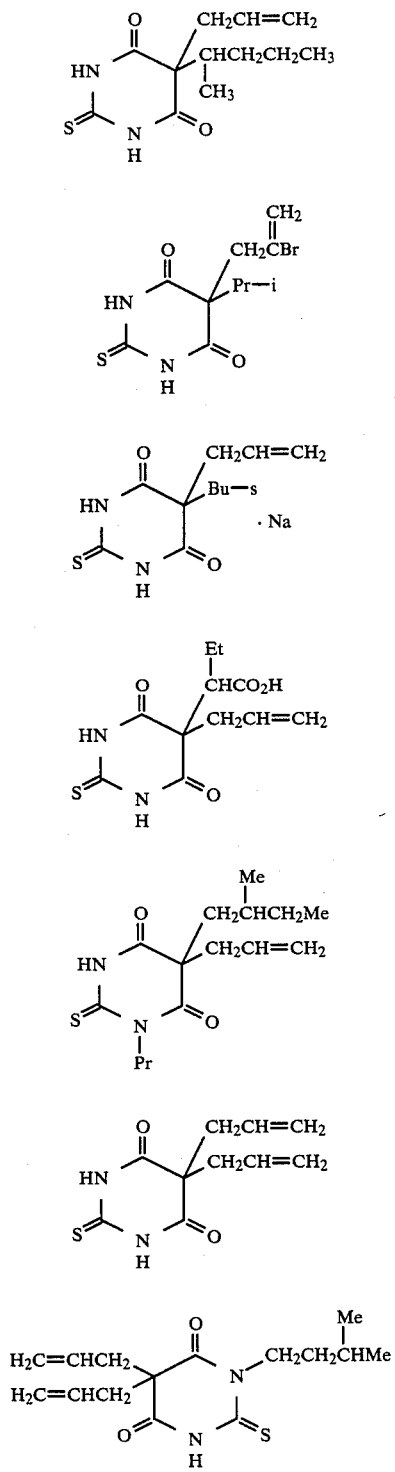

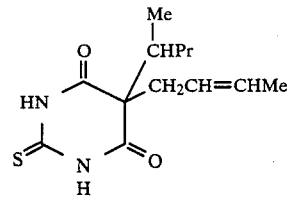

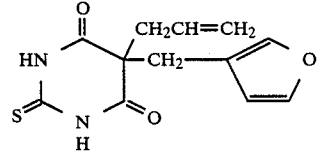

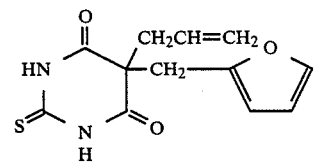

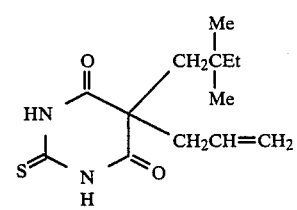

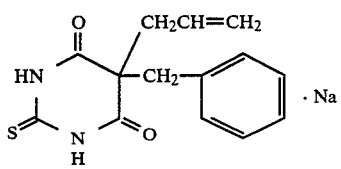

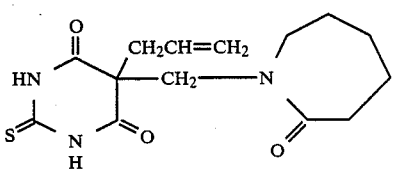

Methods of synthesis of these allyl-containing thiobarbiturates and other substituted thiobarbiturates are known. For example, see M. Michman, et al., *J. Chem. Soc., Perkin Trans.*, 1, 15, 1710–14 (1977). Some of these thiobarbiturates, e.g., thiamylal, are available from commercial sources (Aldrich Chemical Co., Milwaukee, Wis.; Sigma Chemical Co., St. Louis, Mo.).

EXPERIMENTAL

A 15-day old chick embryo retina, incubated for 30 min. in a balanced salt solution (BSS) containing 1 mM Glu, developed a full lesion resembling that described in the immature mouse retina following s.c. administration of Glu. Other excitotoxin agonists also produce acute lesions within 30 min., each agent being effective at a concentration proportional to its known excitatory and toxic potencies. The pattern of cellular degeneration is restricted in each case to the ganglion cell, inner plexiform and inner nuclear layers, but within these areas certain agonists induce different patterns of degeneration, the differences being most pronounced between NMA and KA. Four agonists were employed in the present test, each at a concentration established previously to be the lowest concentration required to consistently cause a fully-developed retinal lesion: KA (25 uM), Quis (50 uM), NMA (200 uM) and Glu (1000 uM). Barbiturates and other antagonists were tested at various concentrations for their ability to prevent KA, Quis, NMA or Glu neurotoxicity. Although partial blocking was observed for each antagonist at concentrations below the threshold for complete protection, the criterion used for comparing agents for antagonist potency was the concentration required to completely prevent KA, Quis, NMA or Glu from exerting any toxic activity in any specimen (n>6) studied at that concentration. Internal controls in each experiment consisted of at least six specimens being incubated with agonist alone. A typical toxic reaction had to be present in all controls and absent from all experimental specimens in order to qualify as a blocking effect. The method of tissue preparation was as follows: 15-day old chick embryos were decapitated and their eyes removed and cut into quadrants after excising the cornea and removing the lens, vitreous and iris. The retinal quadrants were then gently separated from the pigment epithelium and incubated for 30 min. at 37° C. in BSS to which an agonist or agonist plus antagonist was added. The BSS contained 140 mM Na+, 5.0 mM K+, 0.5 mM Ca++, 4.5 mM Mg++, 150 mM Cl−, 5.6 mM glucose and bicarbonate/phosphate buffer (pH 7.3). After incubation for 30 min., the retinal quadrants were fixed by immersion in phosphate-buffered solution containing 1.5% glutaraldehyde and 1% paraformaldehyde, then additionally fixed in 1% osmium tetroxide, dehydrated in graded ethanols, cleared in toluene and embedded in araldite. Sections were cut 1 uM thick on a Sorval ultratome and stained with Methylene blue/Azure 11 for histopathological evaluation by light microscopy.

SEIZURES AND SEIZURE-RELATED BRAIN DAMAGE (SRBD)

Administration of KA (12 mg/kg s.c.) invariably causes a syndrome of status limbic epilepticus and SRBD. The status seizure activity is well established within less than 1 hour after KA injection and acute cytopathological changes become evident in several brain regions (amygdala, piriform cortex, hippocampus, lateral septum and several thalamic nuclei) after persistent seizures have occurred for up to one hour. Effective anticonvulsant protection against the seizures also prevents the brain damage. In the present study, adult male rats (260-325 gm) were given KA (12 mg/kg s.c.) and observed for pre-ictal and ictal behaviors for four hours, then anesthetized with halothane and sacrificed by intracardiac perfusion fixation with 1% paraformaldehyde/1.5% glutaraldehyde in phosphate buffer. The perfused brains were removed from the skulls, sliced in 1 mm thick transverse slabs and additionally fixed in osmium tetroxide, then dehydrated in graded ethanols, cleared in toluene, embedded in araldite and sectioned for light or electron microscopy.

In Table 1, the short-acting barbiturates, methohexital, thiopental and thiamylal are compared with various previously studied agents for potency in protecting the chick embryo retina against NMA, KA or Glu excitotoxic damage. Thiamylal is the most potent compound tested in blocking the actions of NMA, KA or Glu. Methohexital is as potent as the thiobarbiturates in blocking NMA toxicity but is almost devoid of blocking action against KA or Glu.

Exceedingly potent antagonists of NMA are relatively impotent in blocking the toxic action of Glu on retinal neurons. Mixed antagonists that block both NMA and non-NMA receptors are effective against Glu in direct proportion to their efficacy against the non-NMA sites (Table 1). Of all the agents examined, thiamylal is the most potent antagonist at non-NMA (i.e., KA and Quis) sites and it is the most potent antagonist of Glu. Among the mixed antagonists, thiamylal is also the most potent in blocking NMA retinotoxicity.

In cases where serious, persistent seizures may lead to brain damage, the thiobarbiturates of Formula I may also be useful for therapy to prevent that brain damage [J. W. Olney et al., Excitotoxic mechanisms of epileptic brain damage. In Delgado-Escueta AV, Ward AA, Woodbury DM, Porter RJ (eds): "Advances in Neurology, Vol. 44, Basic Mechanisms of the Epilepsies: Molecular and Cellular Approaches," New York: Raven, pp. 857-878]. In Table 2, the short-acting barbiturates are compared for potency in preventing KA from causing seizures or SRBD in the in vivo rat. Each barbiturate was tested at a single dose selected on the basis of pilot experiments with thiamylal. These experiments revealed 20 mg/kg s.c. to be the lowest effective dose of thiamylal for providing complete protection against both the seizures and brain damage. Comparing the three agents at this dose, thiamylal was 100% effective in preventing brain damage which typically occurs following excessive seizure activity in the animals, while thiopental protected only 50% of the animals and methohexital only 17%. The relative potencies of these agents in protecting against these in vivo effects correlates well with their potencies in protecting against the excitotoxic effects of KA in the ex vivo retina.

TABLE 1

POTENCIES OF ANTAGONISTS IN BLOCKING NMA, KA, QUIS OR GLU NEUROTOXICITY

Compounds were rated according to the minimal concentration (uM) required to provide total protection against NMA (200 uM), KA (25 uM), Quis (50 uM) or Glu (1000 uM). Antagonists were tested over a range of concentrations from 1000 uM downward until a minimal effective concentration was established.

| Potential antagonist | vs NMA | vs KA | vs Quis | Vs Glu |
|---|---|---|---|---|
| Barbiturates | | | | |
| Seconal | 600 | 600 | 750 | 1000 |
| Methohexital | 200 | >1000 | >1000 | >1000 |
| Thiopental | 200 | 400 | 400 | 750 |
| Thiamylal | 50 | 250 | 250 | 400 |
| Mixed EAA Antagonists | | | | |
| Kynurenic acid | 300 | 750 | >1000 | >1000 |
| (±)-Cis-2,3 piperidine dicarboxylate | 500 | >1000 | >1000 | >1000 |
| Gamma-aminomethyl-sulphonate | >1000 | >1000 | >1000 | >1000 |
| Competitive NMA-specific Antagonists | | | | |
| D-2-amino-5-phosphonopentanoate | 25 | >1000 | >1000 | >1000 |
| D-2-amino-5-phosphonoheptanoate | 75 | >1000 | >1000 | >1000 |
| Alpha-aminoadipate | 200 | >1000 | >1000 | >1000 |
| Non-competitive NMA-specific Antagonists | | | | |
| Phencyclidine | 0.5 | >1000 | >1000 | >1000 |
| Ketamine | 5 | >1000 | >1000 | >1000 |
| (±) SKF 10,047 | 10 | >1000 | >1000 | >1000 |
| Cyclazocine | 10 | >1000 | >1000 | >1000 |

TABLE 1-continued

POTENCIES OF ANTAGONISTS IN BLOCKING
NMA, KA, QUIS OR GLU NEUROTOXICITY
Compounds were rated according to the minimal concentration
(uM) required to provide total protection against NMA (200
uM), KA (25 uM), Quis (50 uM) or Glu (1000 uM). Antagonists
were tested over a range of concentrations from 1000 uM
downward until a minimal effective concentration was
established.

| Potential antagonist | vs NMA | vs KA | vs Quis | Vs Glu |
|---|---|---|---|---|
| Pentazocine | 25 | >1000 | >1000 | >1000 |

TABLE 2

EFFICACY OF BARBITURATES IN PREVENTING
KA-INDUCED SEIZURES AND SRBD

| Treatment | Seizures* | Brain damage** |
|---|---|---|
| Saline control | 6/6 | 6/6 |
| Thiamylal | 0/6 | 0/6 |
| Thiopental | 3/6 | 3/6 |
| Methohexital | 5/6 | 5/6 |

*Animals that had 3 or more rearing seizures were rated positive for seizures.
**Animals rated positive for brain damage had conspicuous neuropathological changes in hippocampal and extra-hippocampal sites such as amygdala and piriform cortex. Those rated negative for brain damage sometimes had mild glial edema in the CA-3 hippocampal region but were otherwise free from cytopathological changes.

Table 1 shows comparisons of several short-acting barbiturates for their anti-excitotoxic activity in the chick embryo retina with three groups of known EAA antagonists: (1) Mixed competitive EAA antagonists; (2) competitive NMA-specific antagonists; (3) Non-competitive NMA-specific antagonists. Compared with the powerful anti-NMA actions of agents in groups 2 and 3, the short-acting barbiturates are only moderately potent NMA antagonists. But compared with the mixed EAA antagonists, they are as strong or stronger in antagonizing NMA and are substantially more potent against KA and Glu. Additionally, thiamylal has the ability to penetrate the blood brain barrier relatively easily. The reason for assuming that these agents will be effective as neuro-protective agents in ischemia based on their Glu antagonism in vitro is that Glu is the endogenous excitotoxin thought to be responsible for ischemic brain damage.

Effective protection against Glu excitotoxicity may be a combination of a powerful NMA antagonist and an agent with more broad spectrum anti-EAA properties. Or, possibly the best prophylaxis against anoxic-ischemic damage might be to use only a broad spectrum EAA antagonist (e.g., thiamylal) and keep the patient in a deep coma with high concentrations of such an agent while maintaining vital functions by artificial means.

Administration of thiobarbiturates to humans can be by any technique capable of introducing the compounds into the bloodstream of a human patient, including oral administration and intravenous, intramuscular and subcutaneous injections.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to inhibit neuronal degeneration in mammals induced by anoxia, hypoxia or ischemia, which method comprises treating a mammal susceptible to neurotoxic injury with an effective amount of a thiobarbiturate compound having at least one ring atom substituted with an alkenyl or alkynyl type moiety, said thiobarbiturate compound further characterized in having broad spectrum activity as an antagonist at major neuronal excitatory amino acid receptor sites to inhibit excitotoxic actions at said major receptor sites, wherein said thiobarbiturate compound is of the formula

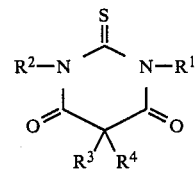

wherein each of $R^1$, $R^2$, $R^3$ and $R^4$ groups is independently selected from hydrido, linear or branched alkyl groups of one to twenty carbon atoms, linear or branched alkenyl groups of two to twenty carbon atoms, linear or branched alkynyl groups of two to twenty carbon atoms, phenyl, benzyl, any one of which $R^1$, $R^2$, $R^3$ and $R^4$ groups may be optionally substituted by oxo, hydroxyl, alkoxy, thio, amino, halo, nitrile, mercapto, carboxyl, carboxamido and thiocarboxamido; and the tautomers, isomers and pharmacologically active salts thereof; with the proviso that at least one of said $R^1$, $R^2$, $R^3$ and $R^4$ groups is an alkenyl or alkynyl group or is a group substituted with at least one alkenyl or alkynyl moiety.

2. The method of claim 1 wherein each of said $R^1$, $R^2$, $R^3$ and $R^4$ groups is independently selected from methyl, ethyl, n-propyl, isopropyl, n-butyl, sec-butyl, iso-butyl, tert-butyl, n-pentyl, iso-pentyl, methylbutyl, dimethylbutyl, neopentyl, alkenyl, alkynyl, hydroxyalkyl, hydroxyalkenyl, hydroxyalkynyl, hydroxphenyl, hydroxybenzyl, alkoxyalkyl, thioalkyl, alkylthioalkyl, thioalkenyl, thioalkynyl, aminoalkyl, aminoalkenyl, aminoalkynyl, phenyl and benzyl, and from haloalkyl, haloalkenyl and haloalkynyl wherein any one or more of the halo atoms may be substituted at any one or more of the alkyl, alkenyl or alkynyl carbon atoms.

3. The method of claim 2 wherein each of said $R^1$ and $R^2$ groups is hydrido and each of said $R^3$ and $R^4$ groups is indenpendently selected from methyl, ethyl, n-propyl, isopropyl, n-butyl, sec-butyl, iso-butyl, tert-butyl, methylbutyl, thiobutyl, ethenyl, propenyl, butenyl, pentenyl, pentynyl, chloroallyl, bromoallyl, 3-chloro-2-butenyl, butoxymethyl, 5-iodo-4-pentenyl, 1-methyl-2-butenyl, 2-(butylthio)ethyl, 3-ethyl-1,2-pentadienyl, 3-hydroxy-1-methylbutyl, isobutoxymethyl, isobutoxymethoxymethyl, 2-mercaptoethyl and 1-methyl-2-pentynyl.

4. The method of claim 3 wherein said thiobarbiturate compound is

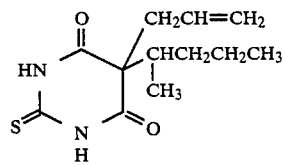

5. The method of claim 4 wherein said thiobarbiturate compound is in the form of the sodium salt.

* * * * *